US008581036B2

(12) United States Patent
Samboju et al.

(10) Patent No.: US 8,581,036 B2
(45) Date of Patent: Nov. 12, 2013

(54) PLANT PEPTIDE GAMMA-ZEIN FOR DELIVERY OF BIOMOLECULES INTO PLANT CELLS

(75) Inventors: Narasimha C. Samboju, Carmel, IN (US); Jayakumar P. Samuel, Carmel, IN (US); Gaofeng Lin, Zionsville, IN (US); Steven R. Webb, Westfield, IN (US); Frank Burroughs, Noblesville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 290 days.

(21) Appl. No.: 13/042,565

(22) Filed: Mar. 8, 2011

(65) Prior Publication Data

US 2011/0247100 A1 Oct. 6, 2011

Related U.S. Application Data

(60) Provisional application No. 61/319,764, filed on Mar. 31, 2010.

(51) Int. Cl.

| | |
|---|---|
| ***C12N 15/82*** | (2006.01) |
| ***C12N 15/87*** | (2006.01) |
| ***C12N 5/00*** | (2006.01) |
| ***C12N 5/02*** | (2006.01) |
| ***C12N 15/29*** | (2006.01) |

(52) U.S. Cl.

USPC ........ 800/278; 435/470; 435/425; 435/430.1; 800/293; 536/23.6

(58) Field of Classification Search

None

See application file for complete search history.

(56) References Cited

U.S. PATENT DOCUMENTS

| | | | | |
|---|---|---|---|---|
| 5,187,267 | A * | 2/1993 | Comai et al. | 800/298 |
| 2009/0104700 | A1 | 4/2009 | Samuel et al. | |
| 2011/0182920 | A2 | 7/2011 | Ugurbil et al. | |

OTHER PUBLICATIONS

Chugh et al. (FEBS Journal 275 (2008), pp. 2403-2414).*

Fernandez-Carneado et al. (Angew. Chem. Int. Ed. (2004), 43, 1811-1814).*

Fittipaldi, Antonio et al., "Transcellular protein transduction using the Tat protein of HIV-1," Advanced Drug Delivery Reviews, 2005, pp. 597-608, vol. 57.

Chen, Chung-Pin et al., "Transfection and expression of plasmid DNA in plant cells by an arginine-rich intracellular delivery peptide without protoplast preparation," FEBS Letters, 2007, pp. 1981-1897, vol. 581.

Terrone, Donato et al., "Penetratin and related cell-penetrating cationic peptides can translocate across lipid bilayers in the presence of a transbilayer potential," Biochemistry Dec. 2, 2003, pp. 13787-13799, vol. 42, No. 47.

Watson, Keith et al., "HIV-1 trans-activating (TAT) protein both a target and a toll in therapeutic approaches," Biochemical Pharmacology, 1999, pp. 1521-1528, vol. 58.

Chang, Microsugar et al., "Cellular internalization of fluorescent proteins via arginine-rich intracellular delivery peptide in plant cells," Plant Cell Physiol., 2005, pp. 482-488, vol. 46, No. 3.

Bicudo, Tatiana C. et al., "Gamma-Zein Secondary Structure in Solution by Circular Dichroism," Biopolymers, pp. 175-178, vol. 89, No. 3 , Dated Nov. 9, 2007.

Mae, Maarja, et al., "Internalisation of cell-penetrating peptides into tobacco protoplasts," Biochemical et Biophysica Acta, 2005, pates 101-107.

Pujals, Silvia, et al., "Proline-rich, amphipathic cell-penetrating peptides," Advanced Drug Delivery Reviews, 2008, pp. 473-484.

Chugh, Archana et al., "Cellular uptake of cell-penetrating peptides PVEC and transportan in plants," Journal of Peptide Science, 2008, pp. 477-481, vol. 14.

Search Report for PCT/US2011/027475, dated Nov. 25, 2011.

Written Opinion for PCT/US2011/027475, dated Nov. 25, 2011.

* cited by examiner

*Primary Examiner* — David T Fox

*Assistant Examiner* — Jared Shapiro

(74) *Attorney, Agent, or Firm* — Ronald S. Maciak; TraskBritt, P.C.

(57) ABSTRACT

A method of introducing a molecule of interest into a plant cell having a cell wall includes interacting a gamma-zein peptide with a molecule of interest to form a gamma-zein linked structure. The gamma-zein linked structure is then placed in contact with the plant cell having a cell wall, and allowing uptake of the gamma-zein linked structure into the plant cell. Alternatively, a gene of interest can be expressed in a plant cell having an intact cell wall by interacting a gamma-zein peptide with the gene of interest to form a gamma-zein linked gene structure, allowing uptake of the gamma-zein linked gene structure into the plant cell, and expressing the gene of interest in the plant cell and its progeny.

20 Claims, 6 Drawing Sheets

SEQUENCE LISTING

```
<160> NUMBER OF SEQ ID NOS: 6

<210> SEQ ID NO 1
<211> LENGTH: 259
<212> TYPE: PRT
<213> ORGANISM: Artificial Sequence
<220> FEATURE:
```

<223> OTHER INFORMATION: Trimer of (VRLPPP) fused to YFP with 6x-His tag

<400> SEQUENCE: 1

```
Met Val Arg Leu Pro Pro Pro Val Arg Leu Pro Pro Pro Val Arg Leu
1               5                   10                  15

Pro Pro Pro His His His His His His Gly Ser Ser Gly Ala Leu Leu
            20                  25                  30

Phe His Gly Lys Ile Pro Tyr Val Val Glu Met Glu Gly Asn Val Asp
        35                  40                  45

Gly His Thr Phe Ser Ile Arg Gly Lys Gly Tyr Gly Asp Ala Ser Val
    50                  55                  60

Gly Lys Val Asp Ala Gln Phe Ile Cys Thr Thr Gly Asp Val Pro Val
65                  70                  75                  80

Pro Trp Ser Thr Leu Val Thr Thr Leu Thr Tyr Gly Ala Gln Cys Phe
                85                  90                  95

Ala Lys Tyr Gly Pro Glu Leu Lys Asp Phe Tyr Lys Ser Cys Met Pro
            100                 105                 110

Asp Gly Tyr Val Gln Glu Arg Thr Ile Thr Phe Glu Gly Asp Gly Asn
        115                 120                 125

Phe Lys Thr Arg Ala Glu Val Thr Phe Glu Asn Gly Ser Val Tyr Asn
    130                 135                 140

Arg Val Lys Leu Asn Gly Gln Gly Phe Lys Lys Asp Gly His Val Leu
145                 150                 155                 160

Gly Lys Asn Leu Glu Phe Asn Phe Thr Pro His Cys Leu Tyr Ile Trp
                165                 170                 175

Gly Asp Gln Ala Asn His Gly Leu Lys Ser Ala Phe Lys Ile Cys His
            180                 185                 190

Glu Ile Thr Gly Ser Lys Gly Asp Phe Ile Val Ala Asp His Thr Gln
        195                 200                 205

Met Asn Thr Pro Ile Gly Gly Gly Pro Val His Val Pro Glu Tyr His
    210                 215                 220

His Met Ser Tyr His Val Lys Leu Ser Lys Asp Val Thr Asp His Arg
225                 230                 235                 240

Asp Asn Met Ser Leu Lys Glu Thr Val Arg Ala Val Asp Cys Arg Lys
                245                 250                 255

Thr Tyr Leu
```

<210> SEQ ID NO 2
<211> LENGTH: 811
<212> TYPE: DNA
<213> ORGANISM: Artificial Sequence
<220> FEATURE:
<223> OTHER INFORMATION: gamma-zein/YFP fusion gene

<400> SEQUENCE: 2

```
gaactagtaa aaaggagaaa tccatggtgc gtctgcctcc tccagttcgt ctgccacctc      60

ctgtacgtct gccgccaccg caccatcacc accaccacgg ctcctctggt gcgctgctgt     120

tccacggcaa aatcccgtac gtggtggaga tggaaggcaa cgttgatggt catactttta     180

gcatccgtgg caaaggctat ggcgatgcct ctgtcggcaa ggttgatgcg cagttcatct     240

gcaccactgg tgatgttccg gttccatggt ctaccctggt tactaccctg acgtacggtg     300

cgcagtgttt cgctaaatac ggcccggagc tgaaagactt ctacaaatct tgtatgccgg     360

atggttatgt acaggaacgt accatcactt tcgagggtga tggtaacttc aaaacccgtg     420

cggaggttac cttcgaaaac ggcagcgtgt ataaccgtgt taaactgaac ggccagggtt     480
```

-continued

```
tcaagaaaga cggccatgtc ctgggtaaaa acctggaatt caacttcacc ccgcactgtc    540

tgtacatttg gggcgaccaa gctaaccatg gcctgaaatc cgctttcaaa atctgccacg    600

aaatcactgg ttccaaaggt gacttcattg tagcagatca cacccagatg aatactccaa    660

tcggtggcgg tccagttcat gtaccggagt atcatcatat gagctatcac gtgaaactga    720

gcaaggatgt taccgatcac cgcgataata tgagcctgaa agagactgtg cgtgcggtgg    780

actgccgtaa aacgtatctg taactcgagc g                                   811


<210> SEQ ID NO 3
<211> LENGTH: 24
<212> TYPE: DNA
<213> ORGANISM: Artificial Sequence
<220> FEATURE:
<223> OTHER INFORMATION: YFP forward primer

<400> SEQUENCE: 3

tgttccacgg caagatcccc tacg                                            24


<210> SEQ ID NO 4
<211> LENGTH: 24
<212> TYPE: DNA
<213> ORGANISM: Artificial Sequence
<220> FEATURE:
<223> OTHER INFORMATION: YFP reverse primer

<400> SEQUENCE: 4

tattcatctg ggtgtgatcg gcca                                            24


<210> SEQ ID NO 5
<211> LENGTH: 24
<212> TYPE: DNA
<213> ORGANISM: Artificial Sequence
<220> FEATURE:
<223> OTHER INFORMATION: PAT forward primer

<400> SEQUENCE: 5

ggagaggaga ccagttgaga ttag                                            24


<210> SEQ ID NO 6
<211> LENGTH: 24
<212> TYPE: DNA
<213> ORGANISM: Artificial Sequence
<220> FEATURE:
<223> OTHER INFORMATION: PAT reverse primer

<400> SEQUENCE: 6

agatctgggt aactggccta actg                                            24
```

PLANT PEPTIDE GAMMA-ZEIN FOR DELIVERY OF BIOMOLECULES INTO PLANT CELLS

CROSS-REFERENCE TO RELATED APPLICATION

This application claims the benefit of U.S. Provisional Patent Application Ser. No. 61/319,764, filed Mar. 31, 2010, the disclosure of which is hereby incorporated herein in its entirety by this reference.

BACKGROUND OF THE INVENTION

Traditional plant breeding strategies to develop new lines of plants that exhibit particular traits are time consuming and sometimes unpredictable. Existing strategies, such as *Agrobacterium*-mediated transformation and particle bombardment depend heavily on the tissue and genotype. Cell penetrating peptides (CPPs) are a novel and fast growing class of short peptides that are known to play an important role in translocation of a wide range of cargo complexes including DNA, RNA and proteins across the cell membranes in mammalian and human cell lines (Schwartz and Zhang, 2000; Langel, 2002; Vives, 2002).

While CPPs have been shown to facilitate cargo delivery in mammalian cells, the use of CPP in plant cells for transfection studies has been limited by a number of factors. A major obstacle to adapting this technology to plants is that, unlike animal cells, plant cells present a dual barrier system (cell wall and plasma membrane) for the internalization of CPPs and their cargos. Therefore, CPPs must overcome these two barriers for efficient translocation of cargo molecules into intact plant cells. CPPs have been used in plant cells but have relied on the use of permeabilization agents to effectuate the delivery of cargo molecules into intact plant cells. CPP-mediated delivery of small molecules, nucleic acids and proteins into intact plant cells remains largely unexplored and is advantageous for in vitro and in vivo genetic and biochemical manipulations in plant systems.

Nanoparticles have unique properties that have been exploited for use in the delivery of DNA to cells. Metal nanoparticles, such as gold (Au) nanoparticles have been used for DNA delivery because of their low cytotoxicity and ease of functionalization with various ligands of biological significance. In addition to metal nanoparticles, semi-conductor nanoparticles (e.g., quantum dots) ("QD") within the size range of 3-5 nm have also been used as carriers to deliver molecules into cells. DNA and proteins can be linked to the ligand attached to the QD via various surface functionalizations (see, e.g. Patolsky, F. et al., J. Am. Chem. Soc. 125, 13918 (2003)).

Nanoparticles have been used to deliver plasmid DNA to a variety of animal cells. It has been found that when DNA coated nanoparticles are incubated with cells not having a cell wall, the cells take up the nanoparticles and begin expressing any genes encoded on the DNA. However, the contemporary plant gene delivery is challenging due to the presence of plant cell walls, which leads to the common reliance on invasive delivery means for genetic transformation of plants. Where nanoparticles delivery to cells normally having a cell wall is desired, the cell's wall is stripped before the addition of the particles to protoplasts of plant (see, Torney, F. et al., Nature Nanotechnol. 2, (2007)). In plant cells, the cell wall presents a formidable barrier for the delivery of exogenously applied molecules. Many invasive methods, like gene gun (biolistics), microinjection, electroporation, and *Agrobacterium*, have been employed to achieve gene and small molecule delivery into walled plant cells, but delivery of proteins has only been achieved by microinjection.

With the ever-growing information from the plant genome-sequencing projects there is an urgent need for a fast, universal (tissue/genotype independent) method in plants for functional genomic studies of a wide array of genes and for the development of transgenic plants expressing important agronomic traits.

BRIEF SUMMARY OF THE INVENTION

The following embodiments are described in conjunction with systems, tools and methods, which are meant to be exemplary and illustrative, and not limiting in scope.

One embodiment of the present invention relates to a method of introducing a molecule of interest into a plant cell having a cell wall. The method includes providing the plant cell having a cell wall and interacting a gamma-zein peptide with a molecule of interest to form a gamma-zein linked structure. The cell having a cell wall and the gamma-zein linked structure are then placed in contact with each other and uptake of the gamma-zein linked molecule of interest into the cell having the cell wall are allowed.

Another embodiment of the invention relates to a method of expressing a gene, the method including providing a plant cell having a cell wall and interacting a gamma-zein peptide with a gene of interest to form a gamma-zein linked gene structure. The plant cell having a cell wall and the a gamma-zein linked structure are placed in contact with each other and uptake of the gamma-zein peptide and the gene into the plant cell comprising a cell wall is allowed. The gene in progeny of a plant having the plant cell is then expressed.

In yet another embodiment of the invention, a molecular substance is transferred into a plant cell. The method includes interacting a gamma-zein peptide with a plasmid DNA to form gamma-zein linked structure. The gamma-zein linked structure is placed in contact with an intact wall-bearing plant cell under conditions permitting the uptake of the gamma-zein peptide and a gene from the plasmid DNA into the plant cell.

In addition to the exemplary aspects and embodiments described above, further aspects and embodiments will become apparent in view of the following descriptions.

DETAILED DESCRIPTION OF THE INVENTION

Figure 1:
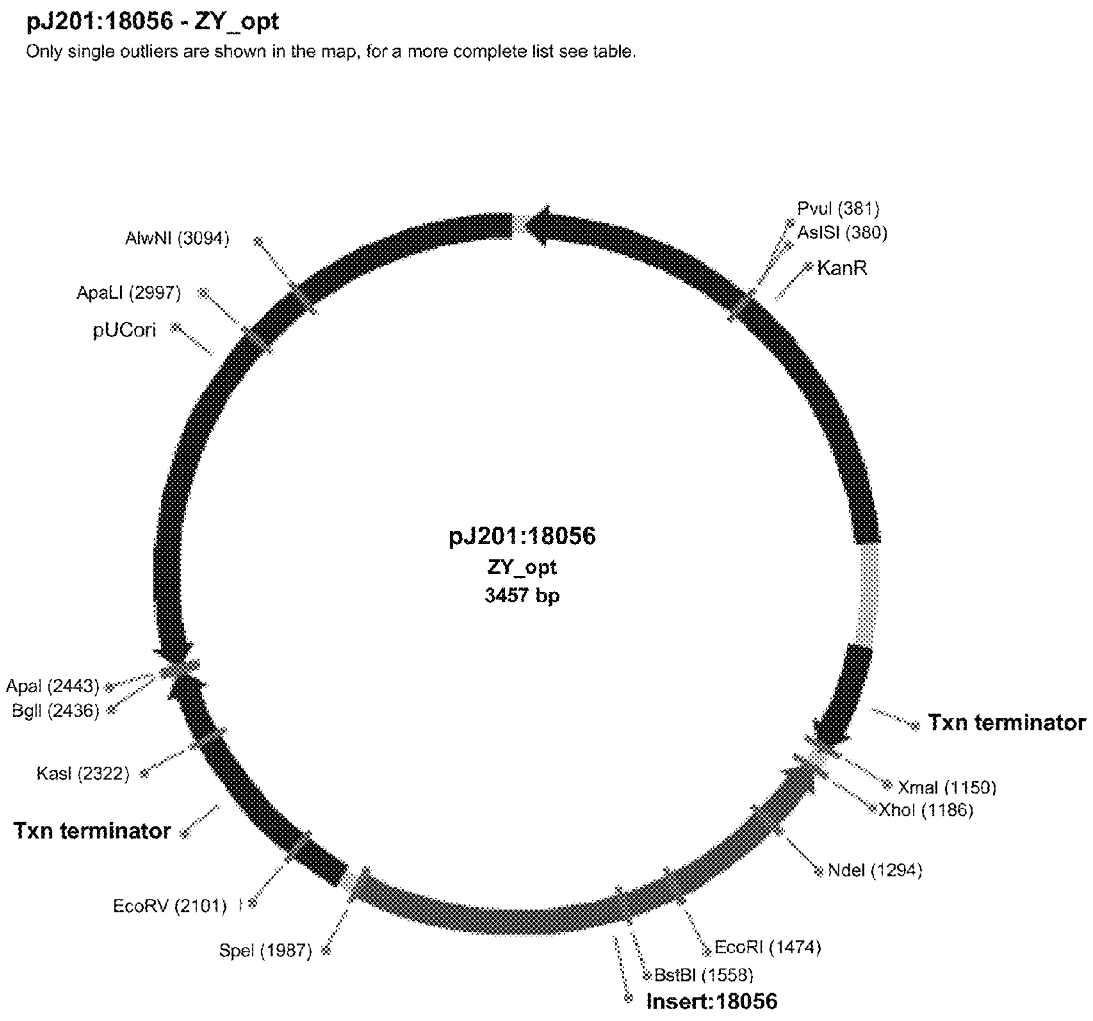
FIG. 1 shows a plasmid map of gamma-zein/YFP fusion gene.

In the description and tables, which follow, a number of terms are used. In order to provide a clear and consistent understanding of the specification and claims, including the scope to be given such terms, the following definitions are provided:

Backcrossing. Backcrossing is a process in which a breeder repeatedly crosses hybrid progeny back to one of the parents, for example, a first generation hybrid $F_1$ with one of the parental genotypes of the $F_1$ hybrid.

Embryo. The embryo may be the small plant contained within a mature seed.

Zein. Zein is a maize protein produced from corn gluten meal. It lacks the amino acids lysine and tryptophan, so it is not suitable as a sole source of dietary protein. It is insoluble in water and alcohols but is soluble in aqueous alcohols, glycols, and glycol ethers. It functions as a film and coating to provide a moisture barrier for nuts and grain products. It also functions as a coating for confections and a glaze for panned goods.

Nanoparticle. A microscopic particle with at least one nanoscale dimension, usually less than 100 nm. Nanoparticles suitable for use in the present invention may have a size range of 1 nm-0.4 um. A quantum dot may have a median diameter ranging from 1-10 nm, preferably 2-4 nm. The nanoparticle may be selected from: gold nanoparticles, gold-coated nanoparticles, porous nanoparticles, mesoporous nanoparticles, silica nanoparticles, polymer nanoparticles, tungsten nanoparticles, gelatin nanoparticles, nanoshells, nanocores, nanospheres, nanorods, magnetic nanoparticles, and combinations thereof.

Quantum dot. A quantum dot is a semiconductor nanostructure that confines the motion of conduction band electrons, valence band holes, or excitons (bound pairs of conduction band electrons and valence band holes) in all three spatial directions. The confinement can be due to electrostatic potentials (generated by external electrodes, doping, strain impurities), the presence of an interface between different semiconductor materials (e.g. in core-shell nanocrystal systems), the presence of the semiconductor surface (e.g. semiconductor nanocrystal), or a combination of these. A quantum dot can have a discrete quantized energy spectrum. The corresponding wave functions are spatially localized within the quantum dot, but extend over many periods of the crystal lattice. A quantum dot contains a small finite number (of the order of 1-100) of conduction band electrons, valence band holes, or excitons (i.e., a finite number of elementary electric charges).

Stabilized or stable transformants. Stabilized or stable transformants refers to a plant whose genome is reproducibly passed from one generation to the next generation.

Uptake. Uptake refers to the translocation of a particle, such as a gamma-zein, across a cell wall or a cellular membrane, wherein the translocation does not occur solely as a result of momentum imparted to the particle by something other than the cell into which the particle is being uptaken. For purposes of comparison, examples of devices or methods, which cause translocation of a particle across a cell wall or a cell membrane solely as a result of momentum imparted to the particle, are biolistic, gene gun, microinjection, and/or impalefection technologies.

In a particular embodiment, the invention relates to use of gamma-zein as a CPP to efficiently deliver payloads into intact plant cells for applications in small molecule delivery, biomolecule delivery, gene delivery, imaging, and various biotechnological diagnostics and sensing functions in plant systems.

In other embodiments of the invention, an “added” or “guest” molecule may be coupled to a gamma-zein molecule. This property can be employed, for example, in specific targeting and editing of molecular sites within cells for areas such as biomimetics, targeted deliveries, for non-genetically modified organism options, and transient transformation options in a variety of tree, vegetable and row crops for trait and disease resistance applications. Embodiments of the invention can also be employed to develop suitable bio-sensors in plants.

According to embodiments the invention, there may be provided a method of introducing a molecule of interest into a plant cell comprising a cell wall, the method comprising placing a gamma-zein containing a molecule of interest in contact with the plant cell and allowing uptake of the gamma-zein across the plant cell wall. In particular aspects of invention, the gamma-zein may reversibly or irreversibly contain, may interact with, or otherwise be bound to and/or carry a molecule of interest.

According to embodiments of the present invention, a plant cell having a cell wall may be any plant cell comprising an intact and whole cell wall. Examples of cells having a cell wall include, but are not limited to, algal, tobacco, carrot, maize, canola, rapeseed, cotton, palm, peanut, soybean, sugarcane, *Oryza* sp., *Arabidopsis* sp., and *Ricinus* sp., preferably tobacco, carrots maize, cotton, canola, soybean and sugarcane; more preferably tobacco and carrots. Embodiments of the invention may include cells comprising a cell wall from any tissue or wherever they are found, including but not limited to, in embryos, meristematic cells, callus, pollen, leaves, anthers, roots, root tips, flowers, seeds, pods, stems, tissue culture and suspensions intact single plant cells.

In embodiments of the invention, a molecule of interest may be any molecule that can be delivered to a plant cell according to the present invention. Molecules of interest, or components of molecules of interest, may comprise, but are not limited to any small molecule, nucleic acids, DNA, RNA, RNAi, miRNA molecules, genes, plasmids, cosmids, YACs, BACs, polypeptides, enzymes, hormones, glyco-peptides, sugars, fats, signaling peptides, antibodies, vitamins, messengers, second messengers, amino acids, cAMP, drugs, herbicides, fungicides, antibiotics, and/or combinations thereof.

Embodiments of the invention include methods for the prevention or treatment of disease. Non-limiting example embodiments include the delivery of fungicides, antibiotics, and/or other drugs to cells in need thereof using methods of the present invention.

In aspects of the invention, the gamma-zein linked structure may be taken up into a variety of plant cell organelles. Examples of locations that gamma-zein linked structures may be taken up include, but are not limited to, cytosol, nucleus, tonoplasts, plastids, etioplasts, chromoplasts, leucoplasts, elaioplasts, proteinoplasts, amyloplasts, chloroplasts, and the lumen of a double membranes. In other embodiments of the invention, gamma-zein linked structure uptake into a cell comprising a cell wall may occur via the symplastic or apoplastic pathway.

Additional embodiments of the invention include genetically modified plant cells and methods for generating them, wherein the plant cells have one or more nucleic acids introduced therein via methods of the present invention. In one example of an embodiment, a plasmid comprising a gene of interest and a selectable marker may be in introduced into a plant cell having a cell wall via a gamma-zein according to the present invention. In further embodiments, stable transformants may be selected that have stably integrated the gene of interest and/or the selectable marker. In alternative embodiments, a plant cell now comprising the gene of interest may be propagated to produce other cells comprising a molecule of interest. In other embodiments, plant cells now comprising a molecule of interest may be a regenerable cell that may be used to regenerate a whole plant including the molecule of interest.

In another aspect, the present invention provides methods of creating regenerable plant cells comprising a molecule of interest for use in tissue culture. The tissue culture will preferably be capable of regenerating plants having substantially the same genotype as the regenerable cells. The regenerable cells in such tissue cultures can be embryos, protoplasts, meristematic cells, callus, pollen, leaves, anthers, roots, root tips, flowers, seeds, pods or stems. Still further, an embodiment of the invention provides plants regenerated from the tissue cultures of the invention.

Alternatively, the present invention provides a method of introducing a desired trait into a plant cell having a cell wall, wherein the method comprises: placing a gamma-zein gene of interest capable of providing the desired trait into the plant cell having a cell wall and allowing uptake of the gamma-zein linked gene of interest across the cell wall. Examples of desired traits include, but are not limited to, traits selected from male sterility, herbicide resistance, insect resistance, resistance to bacterial, fungal, and/or viral disease, and traits conferring benefits to the end user such as modified oil profiles, altered starch and fiber content, augmented vitamin and amino acid content and the like.

Further aspects of the invention provide for the methods of generating of stable plant lines comprising a desired molecule or gene of interest, wherein the desired molecule or gene of interest may be first introduced by gamma-zein mediated translocation across a plant cell wall. Methods of stabilizing genetically, or otherwise altered plant lines are well known to one of ordinary skill in the art and include techniques such as, but not limited to, selfing, backcrosses, hybrid production, crosses to stable populations, and the like. All plants and plant cells comprising a desired molecule or gene of interest first introduced into the plant cell (or its predecessors) by gamma-zein mediated transfer across a cell wall are within the scope of this invention. Advantageously, the plant cells comprising a molecule or gene of interest first introduced into the plant or cell (or its predecessors) by gamma-zein mediated transfer across a cell wall can be used in breeding crosses with other, different, plants to produce first generation ($F_1$) hybrid cells, seeds, and/or plants with superior characteristics and phenotypes.

In embodiments wherein the molecule of interest comprises one or more gene(s), the gene(s) may be a dominant or recessive allele. By way of example, the gene(s) will confer such traits as herbicide resistance, insect resistance, resistance for bacterial resistance, fungal resistance, viral disease resistance, male fertility, male sterility, enhanced nutritional quality, and industrial usage.

With the advent of molecular biological techniques that have allowed the isolation and characterization of genes that encode specific protein or RNA products (e.g. RNAi), scientists in the field of plant biology developed a strong interest in engineering the genome of cells to contain and express foreign genes, or additional or modified versions of native or endogenous genes (perhaps driven by different promoters) in order to alter the traits of a cell in a specific manner. Such foreign additional and/or modified genes are referred to herein collectively as "transgenes." Over the last fifteen to twenty years, several methods for producing transgenic plant cells have been developed and, in particular embodiments, the present invention relates to transformed versions of cells and methods of producing them via introducing into a plant cell having a cell wall a transgene via uptake of gamma-zein linked structure across a plant cell wall and membrane. In embodiments of the invention, the transgene may be contained in an expression vector.

Cell transformation may involve the construction of an expression vector encoding a construct that will function in a particular cell. Such a vector may comprise DNA that includes a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to produce transformed cells using transformation methods as described herein to incorporate transgene(s) into the genetic material of a plant cell comprising a cell wall.

Expression Vectors for Uptake Via Gamma-Zein: Marker or Reporter Genes

Expression vectors may include at least one genetic marker, operably linked to a regulatory element (a promoter, for example) that allows transformed cells containing the marker to be either recovered by negative selection (i e, inhibiting growth of cells that do not contain the selectable marker gene) or by positive selection (i.e., screening for the product encoded by the genetic marker). Many selectable marker genes for transformation are well known in the transformation arts and include, for example, genes that code for enzymes that metabolically detoxify a selective chemical agent, which may be an antibiotic or an herbicide, or genes that encode an altered target, which may be insensitive to the inhibitor. A few positive selection methods are also known in the art.

One commonly used selectable marker gene suitable for plant transformation may include the neomycin phosphotransferase II (nptII) gene under the control of plant regulatory signals, which confers resistance to kanamycin. See, e.g., Fraley et al., Proc. Natl. Acad. Sci. U.S.A., 80:4803 (1983). Another commonly used selectable marker gene may be the hygromycin phosphotransferase gene, which confers resistance to the antibiotic hygromycin. See, e.g., Vanden Elzen et al., Plant Mol. Biol., 5:299 (1985).

Additional selectable marker genes of bacterial origin that confer resistance to antibiotics include gentamycin acetyl transferase, streptomycin phosphotransferase, aminoglycoside-3'-adenyl transferase, and the bleomycin resistance determinant. See Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986). Other selectable marker genes confer resistance to herbicides such as glyphosate, glufosinate or bromoxynil. See Comai et al., Nature 317:741-744 (1985), Gordon-Kamm et al., Plant Cell 2:603-618 (1990) and Stalker et al., Science 242:419-423 (1988). Selectable markers that confer tolerance to herbicides include phosphinothricin acetyl transferase (PAT).

Other selectable marker genes suitable for plant transformation are not of bacterial origin. These genes include, for example, mouse dihydrofolate reductase, plant 5-enolpyruvylshikimate-3-phosphate synthase and plant acetolactate synthase. See Eichholtz et al., Somatic Cell Mol. Genet.

13:67 (1987), Shah et al., Science 233:478 (1986), Charest et al., Plant Cell Rep. 8:643 (1990).

Another class of marker genes suitable for plant transformation requires screening of presumptively transformed plant cells rather than direct genetic selection of transformed cells for resistance to a toxic substance, such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening transformed cells include β-glucuronidase (GUS), β-galactosidase, luciferase and chloramphenicol acetyltransferase. See Jefferson, R. A., Plant Mol. Biol. Rep. 5:387 (1987), Teeri et al., EMBO J. 8:343 (1989), Koncz et al., Proc. Natl. Acad. Sci. U.S.A. 84:131 (1987), DeBlock et al., EMBO J. 3:1681 (1984).

Recently, in vivo methods for visualizing GUS activity that do not require destruction of plant tissue have been made available. Molecular Probes publication 2908, Imagene Green™, p. 1-4 (1993) and Naleway et al., J. Cell Biol. 115:151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, genes encoding Fluorescent Proteins (e.g. GFP, EGFP, EBFP, ECFP, and YFP) have been utilized as markers for gene expression in prokaryotic and eukaryotic cells. See Chalfie et al., Science 263:802 (1994). Fluorescent proteins and mutations of fluorescent proteins may be used as screenable markers.

Expression Vectors for Uptake via Gamma-Zein: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA that may be upstream from the start of transcription and that may be involved in recognition and binding of RNA polymerase and other proteins to initiate transcription. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters, which initiate transcription only in certain tissues, are referred to as "tissue-specific." A "cell type" specific promoter primarily drives expression in certain cell types in one or more organs, for example, vascular cells in roots or leaves. An "inducible" promoter may be a promoter, which may be under environmental control. Examples of environmental conditions that may effect transcription by inducible promoters include anaerobic conditions or the presence of light. Tissue-specific, tissue-preferred, cell type specific and inducible promoters constitute the class of "non-constitutive" promoters. A "constitutive" promoter may be a promoter, which may be active under most environmental conditions.

A. Inducible Promoters

An inducible promoter may be operably linked to a gene for expression in a cell. Optionally, the inducible promoter may be operably linked to a nucleotide sequence encoding a signal sequence, which may be operably linked to a gene for expression in a cell. With an inducible promoter, the rate of transcription increases in response to an inducing agent.

Any inducible promoter can be used in the instant invention. See Ward et al., Plant Mol. Biol. 22:361-366 (1993). Exemplary inducible promoters include, but are not limited to: those from the ACEI system that responds to copper (Mett et al., PNAS 90:4567-4571 (1993)); In2 gene from maize that responds to benzenesulfonamide herbicide safeners (Hershey et al., Mol. Gen. Genetics 227:229-237 (1991) and Gatz et al., Mol. Gen. Genetics 243:32-38 (1994)); and Tet repressor from Tn10 (Gatz et al., Mol. Gen. Genetics 227:229-237 (1991)). A particularly useful inducible promoter may be a promoter that responds to an inducing agent to which plants do not normally respond. An exemplary inducible promoter may be the inducible promoter from a steroid hormone gene, the transcriptional activity of which may be induced by a glucocorticosteroid hormone. Schena et al., Proc. Natl. Acad. Sci. U.S.A. 88:0421 (1991).

B. Constitutive Promoters

A constitutive promoter may be operably linked to a gene for expression in a cell or the constitutive promoter may be operably linked to a nucleotide sequence encoding a signal sequence, which may be operably linked to a gene for expression in a cell.

Different constitutive promoters can be utilized in the instant invention. Exemplary constitutive promoters include, but are not limited to: promoters from plant viruses, such as the 35S promoter from CaMV (Odell et al., Nature 313:810-812 (1985)) and the cassava vein mosaic virus (CsVMV) promoter (see, e.g., U.S. Pat. Nos. 7,053,205 and 6,664,384); promoters from rice actin genes (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)); and maize H3 histone (Lepetit et al., Mol. Gen. Genetics 231:276-285 (1992) and Atanassova et al., Plant Journal 2 (3): 291-300 (1992)). The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-Specific or Tissue-Preferred Promoters

A tissue-specific promoter may be operably linked to a gene for expression in a cell. Optionally, the tissue-specific promoter may be operably linked to a nucleotide sequence encoding a signal sequence, which may be operably linked to a gene for expression in a cell. Plants transformed with a gene of interest operably linked to a tissue-specific promoter can produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11): 2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Transport of protein produced by transgenes to a subcellular compartment, such as the chloroplast, vacuole, peroxisome, glyoxysome, cell wall or mitochondrion or for secretion into the apoplast, can be accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein may be ultimately compartmentalized. Alternatively such subcellular compartment targeting proteins can be directly linked to gamma-zein to direct a molecule of interest to the desired subcellular compartment.

The presence of a signal sequence directs a polypeptide to either an intracellular organelle or subcellular compartment, or for secretion to the apoplast. Many signal sequences are known in the art. See, e.g., Becker et al., Plant Mol. Biol. 20:49 (1992), Close, P. S., Master's Thesis, Iowa State University (1993), Knox, C. et al., "Structure and Organization of Two Divergent Alpha-Amylase Genes from Barley", Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon et al., A short amino acid sequence able to specify nuclear location, Cell 39:499-509 (1984), Steifel et al., Expression of a maize cell wall hydroxyproline-rich glycoprotein gene in early leaf and root vascular differentiation, Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants, which are harvested in a conventional manner, and a foreign protein then can be extracted from a tissue of interest or from total biomass. Protein extraction from plant biomass can be accomplished by known methods, which are discussed, for example, by Heney and Orr, Anal. Biochem. 114:92-6 (1981).

In aspects of the invention, the transgenic plant provided for commercial production of foreign protein may be a cell or a plant. In other aspects, the biomass of interest may be seed. For the relatively small number of transgenic plants that show higher levels of expression, a genetic map can be generated primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location may be useful for proprietary protection of a subject transgenic plant. If unauthorized propagation may be undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques.

Likewise, agronomic genes can be expressed in transformed cells or their progeny. More particularly, plants can be genetically engineered via the methods of the invention to express various phenotypes of agronomic interest. Exemplary genes that may be used in this regard include, but are not limited to, those categorized below.

1. Genes that Confer Resistance to Pests or Disease and that Encode:

A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance genes to engineer plants that are resistant to specific pathogen strains. See, e.g., Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (Arabidops RSP2 gene for resistance to *Pseudomonas syringae*).

B) A gene conferring resistance to a pest, such as soybean cyst nematode. See e.g., PCT Application WO 96/30517; PCT Application WO 93/19181.

C) A *Bacillus thuringiensis* protein, a derivative thereof or a synthetic polypeptide modeled thereon. See, e.g., Geiser et al., Gene 48:109 (1986), which discloses the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D) A lectin. See, for example, the disclosure by Van Damme et al., Plant Molec. Biol. 24:25 (1994), who disclose the nucleotide sequences of several *Clivia miniata* mannose-binding lectin genes.

E) A vitamin-binding protein, such as avidin. See PCT application US93/06487. The application teaches the use of avidin and avidin homologues as larvicides against insect pests.

F) An enzyme inhibitor, for example, a protease or proteinase inhibitor or an amylase inhibitor. See, e.g., Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* .alpha.-amylase inhibitor) and U.S. Pat. No. 5,494,813 (Hepher and Atkinson, issued Feb. 27, 1996).

G) An insect-specific hormone or pheromone such as an ecdysteroid or juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

H) An insect-specific peptide or neuropeptide, which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin may be identified in *Diploptera puntata*). See also U.S. Pat. No. 5,266,317 to Tomalski et al., which discloses genes encoding insect-specific, paralytic neurotoxins.

I) An insect-specific venom produced in nature by a snake, a wasp, or any other organism. For example, see Pang et al., Gene 116:165 (1992), for disclosure of heterologous expression in plants of a gene coding for a scorpion insect toxic peptide.

J) An enzyme responsible for a hyperaccumulation of a monoterpene, a sesquiterpene, a steroid, hydroxamic acid, a phenylpropanoid derivative or another non-protein molecule with insecticidal activity.

K) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules, which contain chitinase-encoding sequences, can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

L) A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

M) A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N) A membrane permease, a channel former or a channel blocker. For example, see the disclosure of Jaynes et al., Plant Sci 89:43 (1993), of heterologous expression of a cecropin-β lytic peptide analog to render transgenic tobacco plants resistant to *Pseudomonas solanacearum.*

O) A viral-invasive protein or a complex toxin derived therefrom. For example, the accumulation of viral coat proteins in transformed plant cells imparts resistance to viral infection and/or disease development effected by the virus from which the coat protein gene may be derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P) An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q) A virus-specific antibody. See, for example, Tavladoraki et al., Nature 366:469 (1993), who show that transgenic plants expressing recombinant antibody genes are protected from virus attack.

R) A developmental-arrestive protein produced in nature by a pathogen or a parasite. For example, fungal endo α-1,4-D-polygalacturonases facilitate fungal colonization and plant nutrient release by solubilizing plant cell wall homo-α-1,4-D-galacturonase. See Lamb et al., Bio/Technology 10:1436 (1992). The cloning and characterization of a gene, which encodes a bean endopolygalacturonase-inhibiting protein, may be described by Toubart et al., Plant J. 2:367 (1992).

S) A developmental-arrestive protein produced in nature by a plant. For example, Logemann et al., Bio/Technology 10:305 (1992), have shown that transgenic plants expressing the barley ribosome-inactivating gene have an increased resistance to fungal disease.

2. Genes that Confer Resistance to an Herbicide:

A) An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Mild et al., Theor. Appl. Genet. 80:449 (1990), respectively.

B) Glyphosate (resistance conferred by, e.g., mutant 5-enolpyruvylshikimate-3-phosphate synthase (EPSPs) genes (via the introduction of recombinant nucleic acids and/or various forms of in vivo mutagenesis of native EPSPs genes), aroA genes and glyphosate acetyl transferase (GAT) genes, respectively), other phosphono compounds such as glufosinate (phosphinothricin acetyl transferase (PAT) genes from *Streptomyces* species, including *Streptomyces hygroscopicus* and *Streptomyces viridichromogenes*), and pyridinoxy or phenoxy proprionic acids and cyclohexones (ACCase inhibitor-encoding genes), See, for example, U.S. Pat. No. 4,940,835 to Shah et al., and U.S. Pat. No. 6,248,876 to Barry et al., which disclose nucleotide sequences of forms of EPSPs, which can confer glyphosate resistance to a plant. A DNA molecule encoding a mutant aroA gene can be obtained under ATCC accession number 39256, and the nucleotide sequence of the mutant gene may be disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes, which confer resistance to herbicides such as L-phosphinothricin. The nucleotide sequence of a PAT gene may be provided in European application No. 0 242 246 to Leemans et al., DeGreef et al., Bio/Technology 7:61 (1989), describe the production of transgenic plants that express chimeric bar genes coding for PAT activity. Exemplary of genes conferring resistance to phenoxy proprionic acids and cyclohexones, such as sethoxydim and haloxyfop include the Acc1-S1, Acc1-S2 and Acc1-S3 genes described by Marshall et al., Theor. Appl. Genet. 83:435 (1992). GAT genes capable of conferring glyphosate resistance are described in WO 2005012515 to Castle et al. Genes conferring resistance to 2,4-D, phenoxy proprionic acids and pyridyloxy auxin herbicides are described in WO 2005107437 assigned to Dow AgroSciences LLC.

C) An herbicide that inhibits photosynthesis, such as a triazine (psbA and gs+ genes) or a benzonitrile (nitrilase gene). Przibila, et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, DNA molecules containing these genes are available under ATCC Accession Nos. 53435, 67441, and 67442. Cloning and expression of DNA coding for a glutathione S-transferase may be described by Hayes et al., Biochem. J. 285:173 (1992).

3. Genes that Confer or Contribute to a Value-Added Trait, Such as:

A) Modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992).

B) Decreased phytate content—1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an

*Aspergillus niger* phytase gene. 2) A gene could be introduced that reduced phytate content. In maize for example, this could be accomplished by cloning and then reintroducing DNA associated with the single allele, which may be responsible for maize mutants characterized by low levels of phytic acid. See Raboy et al., Maydica 35:383 (1990).

C) Modified carbohydrate composition effected, for example, by transforming plants with a gene coding for an enzyme that alters the branching pattern of starch. See Shiroza et al., J. Bacteol. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* may be levansucrase gene), Pen et al., Bio/Technology 10:292 (1992) (production of transgenic plants that express *Bacillus licheniform* may be α-amylase), Elliot et al., Plant Molec. Biol. 21:515 (1993) (nucleotide sequences of tomato invertase genes), Sogaard et al., J. Biol. Chem. 268:22480 (1993) (site-directed mutagenesis may be of barley α-amylase gene), and Fisher et al., Plant Physiol. 102:1045 (1993) (maize endosperm starch branching enzyme II).

In particular embodiments of the invention, gamma-zein can be fused to a nanoparticle. The surface of the nanoparticle may be functionalized, which may, for example, allow for targeted uptake or allow for reversible or irreversible binding of other substances to the surface of the nanoparticle. By way of non-limiting example, the surface of a nanoparticle (e.g., gold nanoparticle or quantum dots) might be functionalized with a self-assembled monolayer of, for example, alkanethiolates, which can be further functionalized or derivatized. In a further non-limiting example, the surface of a nanoparticle may be derivatized with linkers which themselves may be further functionalized or derivatized. In one embodiment, a nanoparticle may be PEGylated. In other embodiments, the nanoparticle may comprise, or may be multifunctionalized with, one or more of a core (active or inactive), a steric coat (active or inert), a cleavable linkage, and/or a targeting molecule or ligand. The nanoparticle can be selected from gold nanoparticles, gold-coated nanoparticles, porous nanoparticles, mesoporous nanoparticles, silica nanoparticles, polymer nanoparticles, tungsten nanoparticles, gelatin nanoparticles, nanoshells, nanocores, nanospheres, nanorods, magnetic nanoparticles, and combinations thereof. Likewise, in particular embodiments of the invention, gamma-zein can be fused to a quantum dot.

In aspects of the invention, gamma-zein and the nanoparticle may be uptaken into various parts of cells. Examples of locations that a nanoparticle may be uptaken into include, but are not limited to, cytosol, nucleus, tonoplasts, plastids, etioplasts, chromoplasts, leucoplasts, elaioplasts, proteinoplasts, amyloplasts, chloroplasts, and the lumen of a double membrane. In other embodiments of the invention, nanoparticle uptake into a cell comprising a cell wall may occur via the symplastic or apoplastic pathway. In other aspects of the invention, gamma-zein and the quantum dot may be uptaken into the aforementioned various parts of cells.

EXAMPLES

The present invention is further described in the following examples, which are offered by way of illustration and are not intended to limit the invention in any manner.

Example 1

Construction of Gamma-Zein/YFP Fusion Protein

A DNA sequence encoding a modified *Zea mays* N-terminal region of gamma-zein protein (GenBank Accession# AAL16977.1, GI:16305109) was fused to the N-terminus of the *Philadium* Yellow Fluorescence Protein (YFP) (Evrogen, Moscow, Russia). The gamma-zein motif of six amino acids was modified, wherein the second residue was changed to arginine from histidine. This modification was made to direct the fusion sequence to the nucleus. Arginine has been shown to improve the efficiency of protein translocation into the cytosol and nucleus of a cell. (Mitchell, et al., (2000), *The Journal ofPeptide Research,* 56 (5): 318-325). A trimer of the modified six amino acids (VRLPPP) of the N-terminal region of gamma-zein was fused to YFP. Additionally, a 6×-His tag was placed between the gamma-zein trimer and the YFP coding sequence. The 6×-His motif was added to facilitate protein purification. The amino acid sequence of this fusion protein is presented as SEQ ID NO: 1.

The fusion gene sequence (SEQ ID NO: 2) was chemically synthesized using phosphoramidite chemistry via an automated DNA synthesizer. Chemical synthesis of this sequence was outsourced to DNA2.0 (Menlo Park, Calif.). The sequence was codon optimized for expression in *Escherichia coli* using DNA2.0 proprietary algorithm to produce an "*E. coli* optimized" nucleotide sequence. The algorithm identifies codons that are used infrequently within the desired host organism and replaces these codons with codons that are more frequently used. In addition, the algorithm removes cis-regulatory sequences (e.g. RNase sites, RNA secondary structure, transcription termination sites) and superfluous restriction enzymes. Additional sequences were added to the ends of the gamma-zein/YFP fusion gene to facilitate cloning and expression. A Shine-Dalgarno sequence (Shine J, Dalgarno L (1975). *Nature* 254 (5495): 34-8) and a unique SpeI restriction enzyme site were added to the 5' end of the gene sequence. A unique XhoI restriction enzyme site was added to the 3' end of the gene sequence. The resulting vector was labeled as pJ201:18056 (FIG. 1).

1.1 Construction of pET Expression Vector

The gamma-zein/YFP fusion sequence was cloned into the *E. coli* expression vector pET280 via standard cloning techniques. pET280 is a modified version of the pET28 plasmid (Novagen, Gibbstown, N.J.). The multiple cloning site and ribosome binding site were removed from pET28 thereby creating pET280. A SpeI-XhoI fragment containing the gamma-zein/YFP coding sequence was excised from the pJ201:18056 vector and ligated into corresponding restriction sites of the pET280 expression vector. The resulting plasmid was confirmed via restriction enzyme digestion and sequencing. The plasmid was transformed into BL21 (DE3) *Escherichia coli* competent cells (Invitrogen, Carlsbad, Calif.). Single colonies were isolated and stored as a glycerol stock until further use.

1.2 Expression and Isolation of Gamma-Zein/YFP Fusion Protein

The gamma-zein/YFP fusion protein was induced using the following conditions: cultures containing the pET280/gamma-zein/YFP expression construct grown to an $O.D._{600}$ of 0.6 in 2 liters (L) of Luria-Bertani broth and 50 μg/ml Kanamycin at 25° C. After reaching the desired $O.D._{600}$, the cultures were induced with 0.1 mM IPTG (isopropyl-β-D-thiogalactopyranoside) for 16 hours at 25° C.

Figure 2:
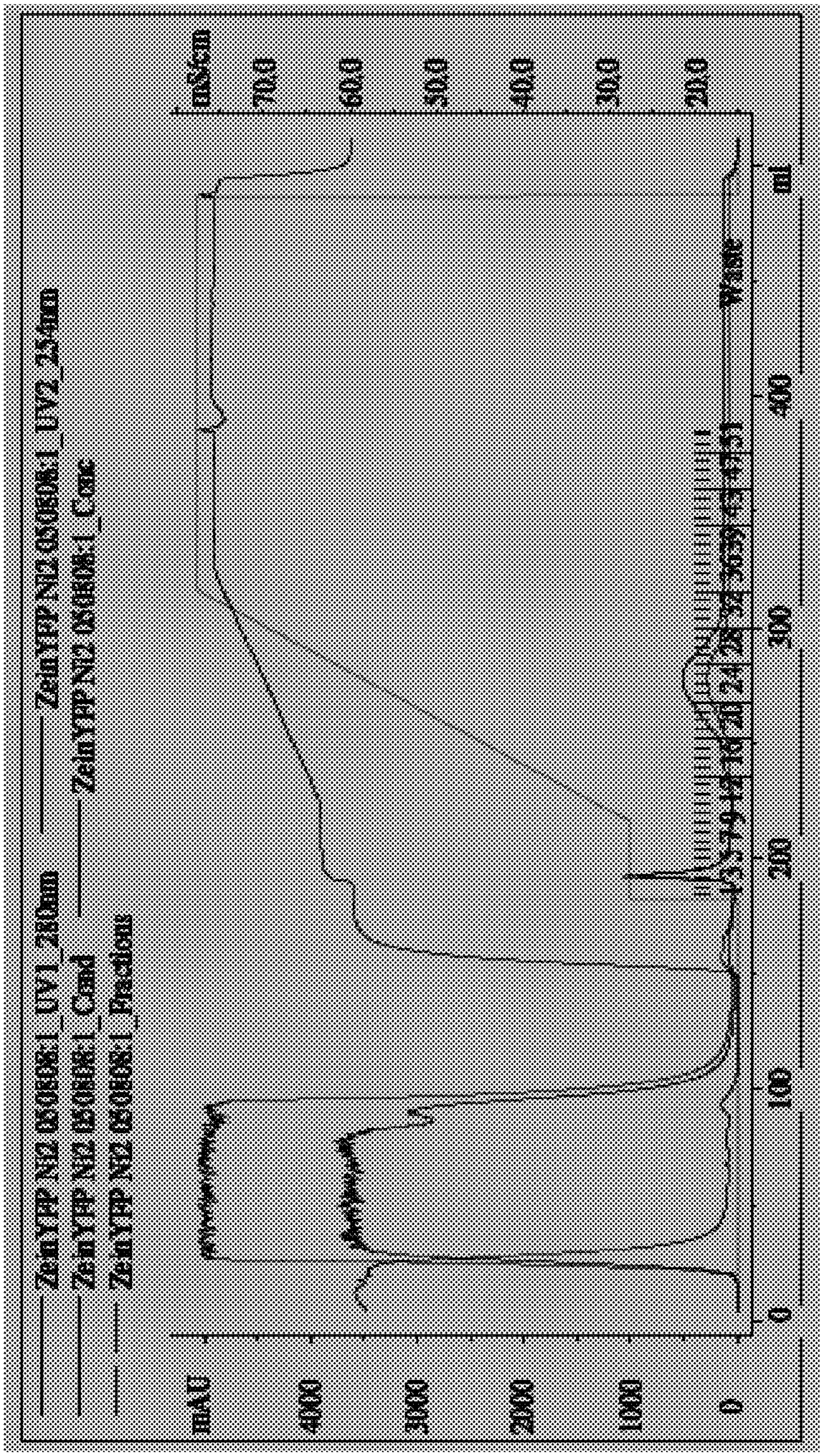
FIG. 2 shows Ni Chelating Chromatography on gamma-zein/YFP fusion peptide purification.

The expressed gamma-zein/YFP fusion protein was isolated and purified. The 2 L cell culture was centrifuged at 24,000×g for 10 minutes and the supernatant was discarded. 5 g of gamma-zein/YFP-containing cell paste was resuspended in 100 ml cold extraction solution (0.5 M NaCl, 5% Glycerol, and 0.5 ml Sigma Protease Inhibitor cocktail (cat# P8849) in PBS). The cells were disrupted on ice using sonication (Branson Sonifier Model 450) for 15 min. The sample was centrifuged at 24,000×g for 20 min at 4° C. and the supernatant was filtered through a 0.45 μm Millipore® filtration device. Imidazole was added to the sample to a final concentration of 10 mM. The gamma-zein/YFP-containing lysate was loaded at 5 ml/min onto a tandem 2×5 ml His-Trap™ column (GE/Pharmacia, cat#17-5248-02) using the a Akt™ Explorer 100 system (GE'Pharmacia). The column was washed with buffer A (0.5 M NaCl, 10 mM Imidazole in PBS) until the absorbance of A280 reached a baseline. The column was then washed sequentially with 10% and 20% Buffer B (0.2 M Imidazole in buffer A) at volumes of approximately 4× column volume (CV). Sample was eluted with 20-100% Buffer B over 10-15 CV and 4 ml fractions were collected (FIG. 2).

1.3 SDS-PAGE Analysis

Figure 3:
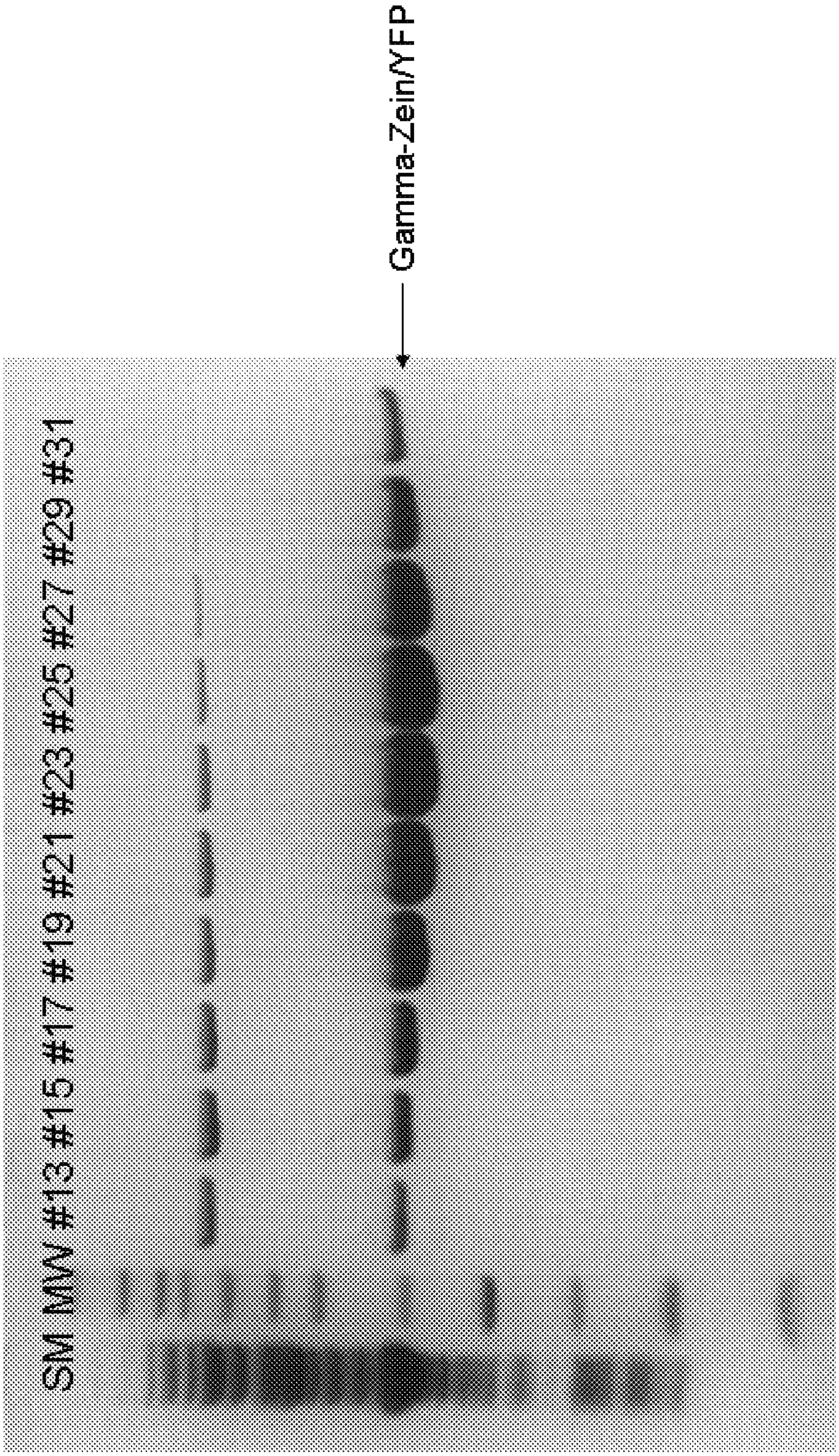
FIG. 3 shows a SDS-PAGE Analysis of gamma-zein/YFP Elution Profile.

A protein gel was run to visualize the fractionated protein. 10-20 μl of each sample was loaded onto a pre-cast 10% Bis-Tris SDS-PAGE gel (Invitrogen, cat# NP0302BOX) for electrophoresis using the XCell SureLock™ Mini-Cell (Invitrogen, cat# EI0001). The samples were run for 35 minutes at 200V in MES-SDS running buffer (Invitrogen, cat# NP0002). The gel was stained with Coomassie Blue R-250 (Bio-Rad, cat#161-0436), as illustrated in FIG. 3. Fractions containing gamma-zein/YFP samples were pooled and transferred into a Millipore Spin column with 10 kDa MWCO, and centrifuged at 4,000 rpm for 20 minutes at 4° C. using a bench top Eppendorf centrifuge (Model 5810R). After centrifugation, sterile PBS solution was added up to 15 ml for buffer exchange. This spin and diafiltration process was repeated three times. The pooled gamma-zein/YFP samples were transferred into a SnakeSkin™ pleated dialysis tubing (Thermo Scientific, cat#68100) with a 10 kDa MWCO, and dialyzed against 2 L of PBS at 4° C. overnight to remove imidazole residues. Protein concentrations were determined using the Bradford assay (Bio-Rad, cat#500-0006) with a Bovine Serum Albumin (BSA) standard (FIG. 3).

1.4 Maldi-TPF Peptide Mass Fingerprinting

Figure 4:
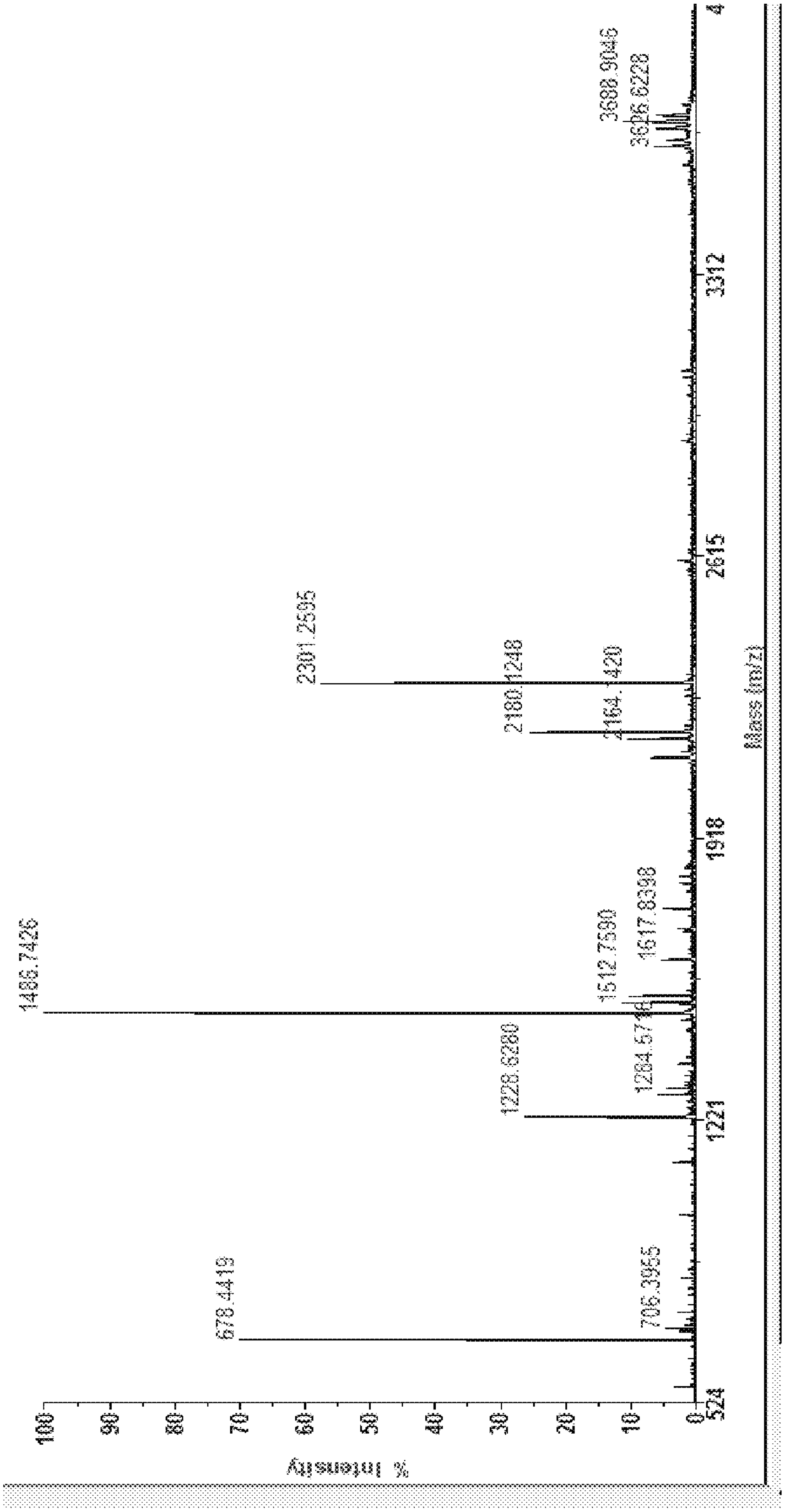
FIG. 4 shows a Maldi-TOF Peptide Mass Spectrum of gamma-zein/YFP.

The 1 μg protein band from the SDS-PAGE gel (approximately 1 μg) was excised and dried in 25% Acetonitrile with 12.5 mM Ammonium bicarbonate in a Speed-Vac. The protein was digested by Trypsin (12.5 ng/μl) at 37° C. during an overnight incubation. Peptides were purified using a C18 Zip Tip (Millipore, cat#2TC18S096) following manufacturer's instructions. Mass spectral analyses was performed using a Voyager Biospectrometry (PerSeptive Biosystems, model DE STR), and mass spectra were collected in the positive ion reflector mode (FIG. 4). The data were input into analysis program PAWS (Proteometrics Inc.) to search for peptide identity.

Example 2

Preparation of Single Cell Plant Material 2.1 JTNT1 Cells

JTNT1 cells are photoautotrophic cells isolated from tobacco. Three to four days prior to transformation, a suspension culture was subcultured to fresh medium by transfer of 2 ml of JTN1 cells into 40 ml of NT1B or LSBY2 media containing 50 nM DAS-PMTI-1 (a microtubule inhibitor) and 0.5-0.1% (v/v) DMSO in a 250-ml flask. Single cells were collected either at four days or seven days after the microtubule inhibitor treatment (as described in, for example, WO 2008/083233, the entire content of which are hereby incorporated by reference). The cells were maintained in minimal medium and 5% carbon dioxide. The cells were sub-cultured once every 14 days by transferring 1 ml of suspension at O.D.$_{600}$ 3.0. These cell types were used as target cells for delivery and localization of gamma-zein/YFP fusion peptide.

2.2 Carrot Cells

A regenerable carrot cryopreserved line (D2-40-018) was thawed and cultured in Linsmeier-Skoog (LS) medium (described in Nagata, T., Nemoto, Y., and Hasezawa, S. (1992) Int. Rev. Cyto 132, 1-30). Medium salts were purchased from PhytoTechnology Laboratories, Catalog #L689. An actively growing suspension line was established within a week, and the maintenance line was sub-cultured by transferring 2 ml PCV (packed cell volume) to 58 ml of LSBY2 suspension 20 medium at 28° C. on an orbital shaker (Innova-3300) at 125 rpm under diffused light on a seven day culture cycle. For single cell production, 1 ml PCV of carrot suspension at the stationary phase was added into 30 ml of LS suspension medium with 1 mM Colchicine (Sigma, Catalog #C3915) and cultured for 7 days. The single cells were produced from 3-7 days of cultures and were ready for transformation experiments. The single cells of carrot could be maintained at stationary phase up to 28 days by diluting the cultures at 14 days by adding 60 ml of fresh LS BY2 liquid medium.

Example 3

Gamma-Zein/YFP Fusion Protein Treatment of Cells

The cells were pre-stained with 15 μg Hoechst for 10 min at 37° C. After the incubation period, the excess stain was removed. The cells were centrifuged at 4000 rpm for 5 minutes and the supernatant was discarded. The cells were washed three times with a 1 ml solution of PBS containing 3% sucrose.

The gamma-zein/YFP fusion protein was added at a 50 μM concentration to 1 ml of carrot single cells or JTNT1 cells within an eppendorf tube. The tubes were placed on a shaker at 100 rpm at 25° C. for 60 minutes.

Example 4

Gamma-Zein/YFP Fusion Protein Accumulation Within Plant Cells

Aliquots of 100 μl of the fusion protein/cell mixture were removed at 10 minutes, 30 minutes, and 60 minutes for imaging. The cells were centrifuged at 5,000 rpm for five minutes and washed three times with PBS. Finally the cells were resuspended in 100 μl PBS.

The efficiency of the fusion peptides to internalize and localize into the sub-cellular compartments of the plant cell and tissues was monitored. Cells were imaged on a LSM-Leica™ TCS SP2/UV or Zeiss™ LSM. A high numerical aperture (1.2-1.3) water immersion objective (63×) and a 488 nm or a 514 nm laser line from an argon ion to excite YFP was used.

Figure 5:
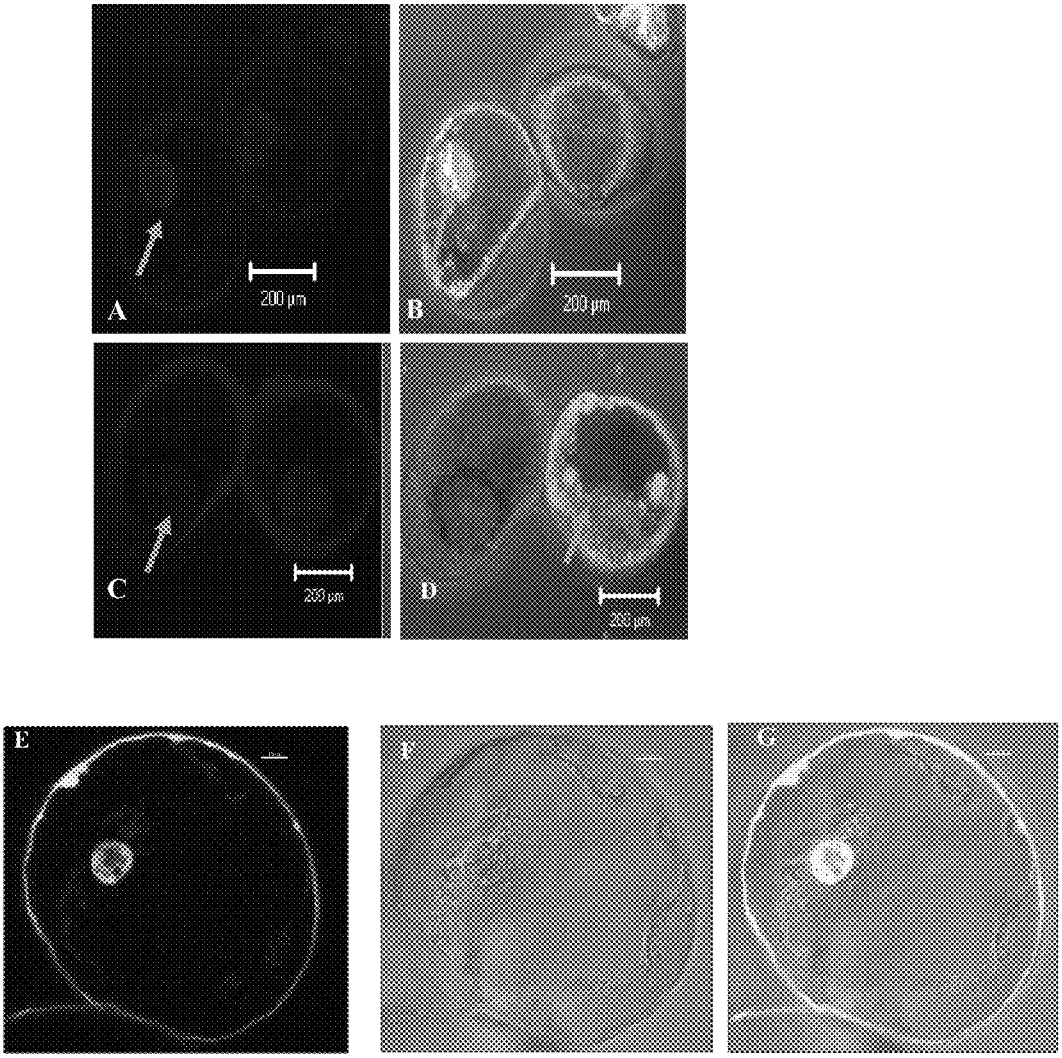
FIG. 5 shows confocal microscopic images illustrating cellular uptake and internalization of fusion peptide: A. Carrot single cell stained with Hoechst 33342 showing nucleus; B. Carrot single cell showing gamma-zein/YFP fluorescence localization in the nucleus and cytoplasm; C. Tobacco JTNTI cells stained with Hoechst 33342 showing nucleus; D. Tobacco JTNT1 cells showing gamma-zein/YFP fluorescence in the nucleus and cytoplasm along with the blue color nuclear staining with Hoechst 33342; E. Confocal image displaying gamma-zein/YFP fusion peptide targeted to both plasma membrane and the nucleus of JTNT1 cells; and F and G showing corresponding bright field images and overlay of confocal/bright field images, respectively.

Confocal and Differential Interference Contrast (DIC) images were captured using 405 nm and 488 nm laser with a 430-480 nm and LP560 nm filters, respectively. The gamma-zein yellow fluorescence signal was shown to localize to the nucleolus and cytoplasm of both the Carrot and JTNT1 single cells after 10 minutes (illustrated in FIG. 5).

Example 5

Figure 6:
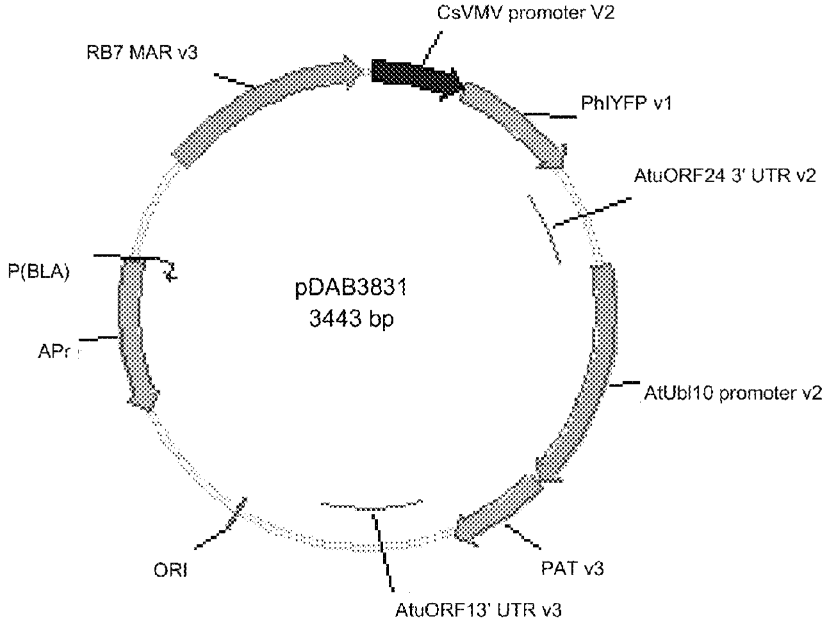
FIG. 6 shows a plasmid map of pDAB3831.

In Plant a Transformation of *Arabidopsis* by Floral Dip with Peptide and Plasmid DNA The purified gamma-zein peptide was mixed with plasmid DNA pDAB3831, illustrated in FIG. 6. 0.25 mg of gamma-zein peptide were added to 0.5 mg of the plasmid DNA and incubated in water for 30 minutes to form a peptide/DNA complex. pDAB3831 contains the PAT selectable marker gene driven by the *Arabidopsis* Ubiquitin 10 Promoter (AtUbi 10) and the *Philadium* Yellow Fluorescence Protein gene (PhiYFP) driven by the Cassava Vein Mosaic Virus Promoter (CsVMV). The gamma-zein peptide/pDAB3831 complex and a separate control experiment of only pDAB3831 plasmid DNA were administered to 4 week-old floral buds of *Arabidopsis thaliana* cv Columbia. 20 mL of the peptide/DNA complex and 20 ml of the DNA control were mixed with infiltration medium (5% sucrose and 0.04% Silwet-77) in a glass trough for 30 seconds. The infiltration medium containing the peptide/DNA solution was used to transform the *Arabidopsis* plants using a modified Clough and Bent protocol. (Clough S J and Bent A F, 1998. Plant J 16:735-43). After dipping the infiltration complex was stored at 4° C. and subsequently used to dip the same plants after two days using the same protocol. Repeating the transformation step was done to increase the transformation frequency.

Plants were covered by a plastic dome to maintain humidity for 24 hours. After 24 hours, the dome was removed and plants were grown normally in a Conviron® (models CMP4030 and CMP3244, Controlled Environments Limited, Winnipeg, Manitoba, Canada) under long day conditions (16 hours light/8 hours dark) at a light intensity of 120-150 μmol/$m^2$/sec under constant temperature (22° C.) and humidity (40-50%), and allowed to mature and produce seed. The T0 seeds were collected and sterilized. Additionally, the seeds were vernalized for two days at 4° C. To select for positive transformants, the seeds were plated on an MS medium (0.43% Murashige and Skoog salt mixture, 2.5 mM 2-[N-morpholino]ethanesulfonic acid, 1× Gamborg's vitamin solution, 0.9% bacto-agar, pH 5.7-5.9) containing 10 μg/ml BASTA and grown in an incubator (22° C., 100 μmole quanta m-2 s-1) for 7-10 days. Putative transformants were identified and transferred to soil and grown to maturity.

Example 6

Molecular Analysis for Transgenes PAT and YFP gDNA from the *Arabidopsis* transgenic plants and gDNA from the *Arabidopsis* ecotype Columbia wild-type control was extracted from leaf material of 6-week-old plants using the Plant DNAZOL kit (Invitrogen Inc). PAT and YFP gene fragments were PCR amplified from only the transgenic plants. The 50 μL PCR reaction mixture contained 100 ng template DNA, 1× ExTaq reaction buffer (TaKaRa Bio), 0.2 mM dNTP, 10 μmol each primer, and 0.025 units/μL ExTaq. The YFP primers are shown as SEQ ID NO: 3 and SEQ ID NO: 4. The PAT primers are shown as SEQ ID NO: 5 and SEQ ID NO: 6. The following PCR cycling conditions were used: 1 cycle at 96° C. for 5 min, 31 cycles of the following PCR program: 94° C., 15 s; 65° C., 30 s; 72° C., 1 min., and a final extension was performed at 72° C. for 7 min to complete product synthesis. The amplified fragments were gel-purified using the QIAquick™ gel extraction kit (Qiagen Inc). The PCR fragments were sequenced using the PAT forward primer (SEQ ID NO:5) and YFP forward primer (SEQ ID NO:3) using advanced Sanger sequencing technology (MWG Biotechnologies, Inc) and the sequences were analyzed using Sequencher™ software.

Example 7

Identification of Homologous Motifs and Mutagenesis of Gamma-Zein Sequence for Improved Protein Translocation Efficiency Additional motifs that are homologous to the gamma-zein domain were identified and are tested for intracellular protein translocation. These sequences were identified from current public databases, such as NCBI (National Center for Biotechnology Information). The gamma-zein sequence was used as the input for the BLAST (Basic Local Alignment Search Tool) (Altschul et al., 1997) algorithm. Using default settings, the sequence was compared against deposited NCBI protein sequences. The search returned several homologous protein sequences. The identified gamma-zein motif is modified to enhance the efficiency of intracellular protein translocation. Various residues of the VRLPPP sequences are changed via site directed mutagenesis protocols. The modified gamma-zein sequences are used for delivering proteins and DNA into plant cells using the protocols described above.

Example 8

Targeting of Cell Organelles Using Chimeric Gamma-Zein Sequence

Additional experiments are conducted to test the peptide targeting of cell organelles via chimeric gamma-zein/cell organelle targeting motifs. In a particular example, the gamma-zein and a chloroplast targeting sequence is fused to the N-terminus of a fluorescent protein, such as YFP. The targeting of the YFP protein to the chloroplast is imaged via fluorescence microscopy. Additional targeting sequences to various other cell organelles (e.g. mitochondria, endoplasmic reticulum, nucleus, etc.) that are known in the art, are fused in conjunction with the gamma-zein sequence and are used to target a specific cell organelle. Either proteins or DNA is targeted to the identified cell organelle.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims and their equivalents.

What may be claimed is:

1. A method of introducing a nucleic acid of interest into a plant cell having an intact cell wall, the method comprising:
   - providing the plant cell having an intact cell wall, wherein said plant cell is within a plant tissue;
   - interacting a gamma-zein peptide with the nucleic acid of interest to form a gamma-zein linked structure;
   - placing the cell having an intact cell wall and the gamma-zein linked structure in contact with each other; and
   - allowing uptake of the gamma-zein linked structure into the cell having the intact cell wall.

2. The method according to claim 1, wherein interacting a gamma-zein peptide with the nucleic acid of interest comprises fusing the nucleic acid of interest with the gamma-zein peptide.

3. The method according to claim 1, further comprising allowing uptake of the gamma-zein linked structure into a compartment of the plant cell comprising an intact cell wall.

4. The method according to claim 3, wherein the compartment is selected from the group consisting of cytosol, nucleus, tonoplasts, plastid, etioplast, chromoplast, leucoplast, elaioplast, proteinoplast, amyloplast, chloroplast, and the lumen of the double membrane.

5. The method according to claim 1, wherein the plant cell comprising an intact cell wall is selected from the group consisting of tobacco, carrot, maize, canola, rapeseed, cotton, palm, peanut, soybean, *Oryza* sp., *Arabidopsis* sp., *Ricinus* sp., and sugarcane cells.

6. The method according to claim 1, wherein the plant cell is from a tissue selected from the group consisting of embryo, meristematic, callus, pollen, leaves, anthers, roots, root tips, flowers, seeds, pods and stems.

7. The method according to claim 1, wherein the gamma-zein peptide comprises SEQ ID NO 1.

8. The method according to claim 1, wherein the nucleic acid of interest comprises a component selected from the group consisting of nucleic acids, DNA, RNA, RNAi molecules, genes, plasmids, cosmids, YACs, BACs, and combinations thereof.

9. The method according to claim 8, wherein the nucleic acid of interest comprises a gene.

10. The method according to claim 9, wherein the gene is a foreign protein gene, an agronomic gene, or a marker gene.

11. The method according to claim 9, further comprising selecting cells that have stably integrated the gene.

12. The method according to claim 11, wherein the selected cells are regenerable cells.

13. The method according to claim 12, further comprising regenerating a fertile plant from the regenerable cells.

14. A method of expressing a gene, the method comprising:

providing a plant cell having an intact cell wall, wherein said plant cell is within a plant tissue;

interacting a gamma-zein peptide with a gene to form a gamma-zein linked structure;

placing the plant cell having an intact cell wall and the gamma-zein linked structure in contact with each other;

allowing uptake of the gamma-zein peptide and the gene into the plant cell comprising an intact cell wall; and expressing the gene in progeny of a plant having the plant cell.

15. The method according to claim 14, wherein the gene is expressed in a chloroplast.

16. The method according to claim 14, further comprising selecting for cells stably expressing the gene.

17. The method according to claim 14, wherein the gamma-zein peptide comprises SEQ ID NO 1.

18. A method for transferring a plasmid DNA into a plant cell, comprising:

interacting a gamma-zein peptide with the plasmid DNA to form a gamma-zein linked structure; and contacting the gamma-zein linked structure with an intact wall-bearing plant cell under conditions permitting the uptake of the gamma-zein peptide and a gene from the plasmid DNA into the plant cell;

wherein said plant cell is within a plant tissue.

19. The method of claim 18, further comprising stably expressing the gene in progeny of a plant having the plant cell.

20. The method according to claim 18, wherein the gamma-zein peptide comprises SEQ ID NO 1.

* * * * *